(12) United States Patent  (10) Patent No.: US 9,186,513 B2
Wengreen et al.  (45) Date of Patent: Nov. 17, 2015

(54) SUBCUTANEOUS CARDIAC MONITORING DEVICES, SYSTEMS AND METHODS

(71) Applicant: Medtronic, Inc., Minneapolis, MN (US)

(72) Inventors: Eric Wengreen, Issaquah, WA (US); Randy S Roles, Elk River, MN (US); John E Lovins, Oakdale, MN (US)

(73) Assignee: Medtronic, Inc., Minneapolis, MN (US)

( * ) Notice: Subject to any disclaimer, the term of this patent is extended or adjusted under 35 U.S.C. 154(b) by 450 days.

(21) Appl. No.: 13/788,823

(22) Filed: Mar. 7, 2013

(65) Prior Publication Data

US 2014/0257072 A1  Sep. 11, 2014

(51) Int. Cl.
| | | |
|---|---|---|
| *A61B 5/04* | (2006.01) | |
| *A61N 1/365* | (2006.01) | |
| *A61N 1/375* | (2006.01) | |
| *A61B 5/042* | (2006.01) | |
| *A61N 1/00* | (2006.01) | |

(52) U.S. Cl.
CPC .............. *A61N 1/365* (2013.01); *A61B 5/0422* (2013.01); *A61N 1/3756* (2013.01); *A61B 2560/063* (2013.01); *A61B 2562/16* (2013.01)

(58) Field of Classification Search
CPC ........... A61B 2018/00214; A61B 2017/00243; A61B 5/042; A61B 5/0422; A61B 5/0452; A61B 5/0031; A61B 5/04011; A61B 5/0402; A61N 1/056; A61N 1/05; A61N 1/057
USPC ................. 600/372–377, 393, 481, 508–513, 600/516–522; 607/115, 119, 121–123, 129
See application file for complete search history.

(56) References Cited

U.S. PATENT DOCUMENTS

| | | | |
|---|---|---|---|
| 5,331,966 | A | 7/1994 | Bennett et al. |
| 5,987,352 | A | 11/1999 | Klein et al. |
| 6,230,059 | B1 | 5/2001 | Duffin |
| 6,600,949 | B1 | 7/2003 | Turcott |
| 7,299,086 | B2 | 11/2007 | McCabe et al. |
| 7,797,036 | B2 | 9/2010 | Zhang et al. |
| 7,894,889 | B2 | 2/2011 | Zhang |
| 2007/0073353 | A1 | 3/2007 | Rooney et al. |
| 2009/0149902 | A1 | 6/2009 | Kumar et al. |

FOREIGN PATENT DOCUMENTS

EP  0657136 A1  6/1995

OTHER PUBLICATIONS (PCT/US20141021568) PCT Notification of Transmittal of the International Search Report and the Written Opinion of the International Searching Authority, Mailed Jun. 24, 2014, 11 pages.

*Primary Examiner* — Joseph Stoklosa
*Assistant Examiner* — Brian M Antiskay

(57) ABSTRACT

An implantable cardiac monitoring device includes first and second arms, pivotably attached to one another; electronic circuitry and an associated power source of the device are hermetically sealed in a housing formed by one of the arms. A first electrode is carried by the first arm, a second electrode by the second arm, and a third electrode by one of the two arms. The device further includes a tether element, preferably a strut, pivotably attached between the arms and movable between a folded state and an expanded state. When the strut is in the folded state, the device, in a relatively compact form, can be inserted through a relatively small incision and into subcutaneous tissue, after which, the strut is moved to the expanded state where ends of the arms are spaced apart from one another and supported by the strut, and the three electrodes form dual sensing vectors.

20 Claims, 8 Drawing Sheets

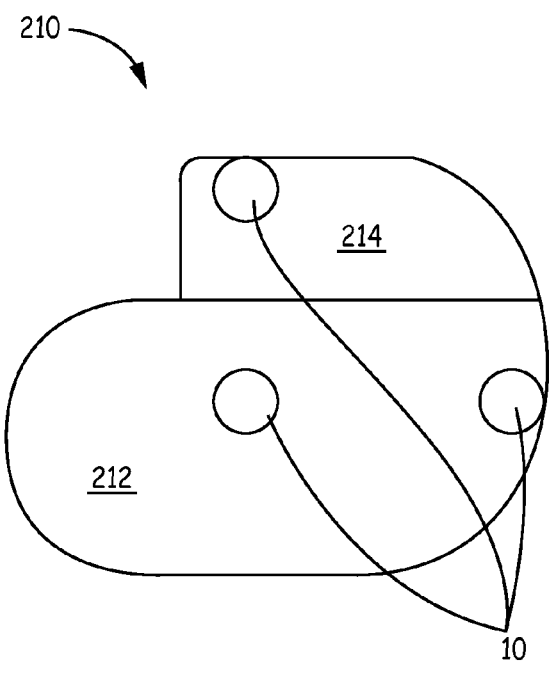
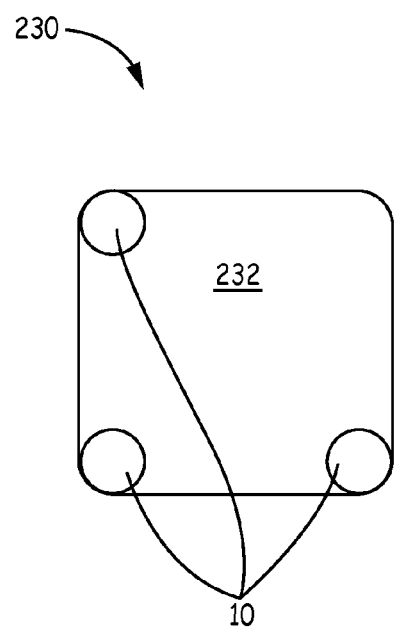
FIG. 2A
FIG. 2B

SUBCUTANEOUS CARDIAC MONITORING DEVICES, SYSTEMS AND METHODS

TECHNICAL FIELD

The present invention pertains to medical devices, systems and methods, and, more specifically, to those providing subcutaneously implanted sensing vectors for cardiac monitoring.

BACKGROUND

A variety of configurations of electrode arrays, which are known in the art, are useful for monitoring electrical activity of the heart by generating electrocardiograms (ECG's), which characterize cycles of cardiac muscle contraction and relaxation as myocardial cells depolarize and then repolarize. Those skilled in the art are familiar with limb leads and precordial leads, which are attached to a patient's skin for generating far-field ECG's, as well as electrode arrays that are included in subcutaneously implantable cardiac monitoring devices and systems for the same purpose.

FIG. 1A is a schematic diagram showing an array of subcutaneously implanted cardiac monitoring electrodes 110, which are configured to create a pair of sensing vectors. FIG. 1B shows portions of two exemplary ECG waveform plots N and I, which may be generated from electrical cardiac signals as sensed by electrodes 110, wherein the sensed signals are projections of the electric force vectors (corresponding to the aforementioned depolarization and repolarization) on each sensing vector of electrodes 110. ECG N represents a typical cardiac cycle, wherein atrial contraction is represented by a P wave, ventricular depolarization by a QRS complex, and ventricular repolarization by a T wave. ECG I represents a cardiac cycle when a portion of the heart muscle may be ischemic as indicated by a deviation in the ST segment. (The ST segment and the deviation therefrom are both indicated with a bold arrow in each plot of FIG. 1B.) A pair of sensing vectors, arranged approximately orthogonal to one another, is preferred in order to reliably detect ST segment deviations, which may be indicative of ischemia in instances of acute myocardial infarction.

FIGS. 2A-B are plan views of two exemplary, prior art implantable medical devices 210, 230, each of which include electrodes 10 arranged in an array similar to that illustrated in FIG. 1A, so as to create a pair of sensing vectors. FIG. 2A illustrates device 210 including a hermetically sealed housing, or can 212, which contains electronic circuitry and an associated power source (not shown), a connector module 214, by which one or more elongate implantable medical electrical leads can be coupled to the circuitry contained within can 212, and electrodes 10 mounted on can 212 or module 214. Those skilled in the art are familiar with implantable pulse generators for cardiac stimulation and sensing, such as device 210, which are typically implanted in a pectoral subcutaneous pocket with the associated electrical leads extending therefrom to either an endocardial location, or an epicardial location. Although the associated electrical leads carry electrodes that may used for monitoring electrical activity of the heart, a far-field ECG generated by subcutaneously located electrodes 10 can provide useful information in a variety of applications. FIG. 2B illustrates device 230, which, like device 210, includes a hermetically sealed housing, or can 232, in which electronic circuitry and a power source are contained, and electrodes 10, all of which are mounted on can 232. Device 230 may be employed solely for cardiac monitoring via electrodes 10 that generate a far-field ECG, for example, from a subcutaneous implant location like that illustrated in FIG. 1A, which is accessed via an incision 15. Those skilled in the art are familiar with other forms of subcutaneously implantable cardiac monitors, for example, the Reveal® device manufactured by Medtronic, Inc. of Minneapolis, Minn.

Recent advances in the fabrication of electronics and associated power sources allow for a significant volume reduction of subcutaneous cardiac monitoring devices, for example, allowing for minimally invasive implant through a relatively small incision. Yet, the smaller volume may not accommodate the necessary spacing of electrodes to create a preferred arrangement of a pair of sensing vectors.

SUMMARY

Embodiments and methods of the present invention provide for subcutaneous cardiac monitoring, wherein device embodiments include sensing electrodes, which are spaced to form dual sensing vectors that are capable of detecting ST segment deviations, when the device is in an implant form, and which can be inserted in a relatively compact form through a relatively small incision. According to embodiments of the present invention, an implantable cardiac monitoring device includes first and second arms, which are pivotably attached to one another, electronic circuitry and an associated power source, which are hermetically sealed in a housing formed by one of the arms, and a tether element attached between the arms, and movable between a folded state and an expanded state; a first electrode of the device is carried by the first arm, a second electrode of the device is carried by the second arm, and a third electrode of the device is carried by one of the first and second arms, such that, when the tether element is in the expanded state, the three electrodes form the dual sensing vectors, preferably arranged orthogonal to one another. According to some preferred embodiments and methods, the tether element is a strut, and the device, in a relatively compact form, with the strut in the folded state, is inserted through an incision and into subcutaneous tissue, after which, the strut is moved to the expanded state to place the device in the implant form, where ends of the arms are spaced apart from one another and supported by the strut. In some embodiments, a flex-segment of the strut includes a spring member biased to move the strut to the expanded state; while in other embodiments a flex-segment of the strut is configured to engage with a tool that is used to pull the flex-segment, and thereby move the strut into the expanded state.

A system, according to some embodiments, includes a tool for holding the device in the relatively compact form, while pushing the device through the incision. The tool, according to some embodiments, includes a rod having a distal end that engages the aforementioned flex-segment of the strut in order to apply the pull force that moves the strut into the expanded state; after which, a torsion force may be applied to the rod to disengage the rod from the flex-segment.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIGS. 2A-B are plan views of two exemplary, prior art implantable medical devices that each include an electrode array;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1B:
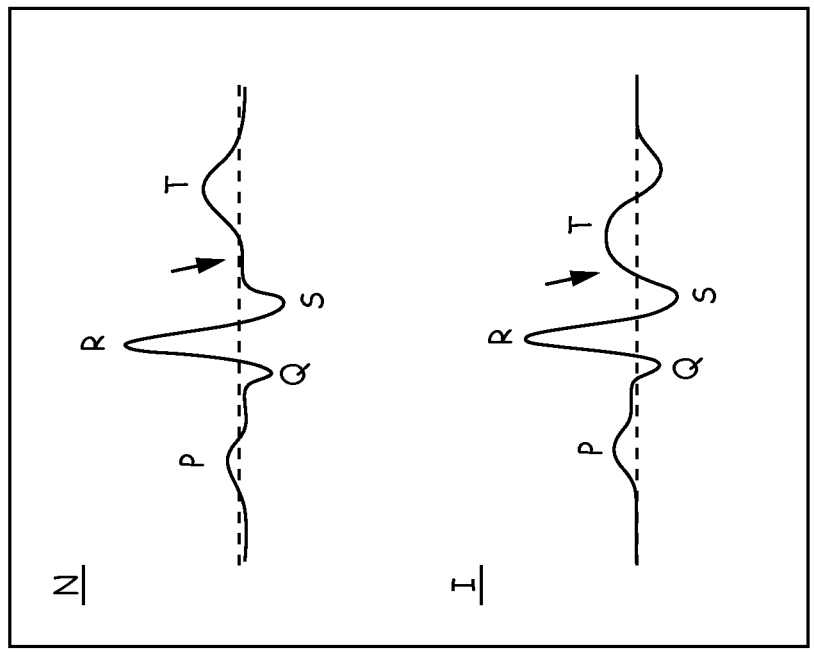
FIG. 1B shows portions of two exemplary electrocardiogram (ECG) waveform plots.
Figure 1A:
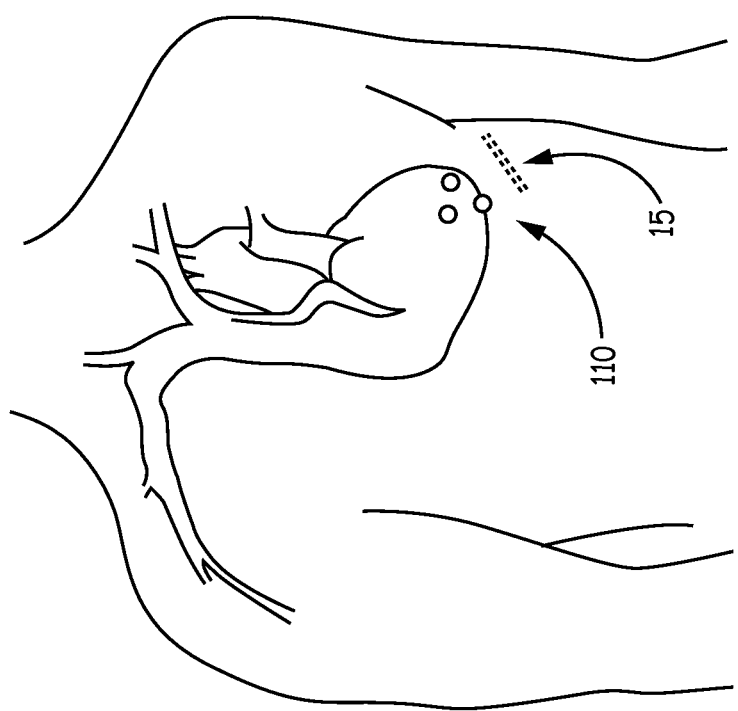
FIG. 1A is a schematic diagram showing subcutaneously implanted cardiac monitoring electrodes.
Figure 3A:
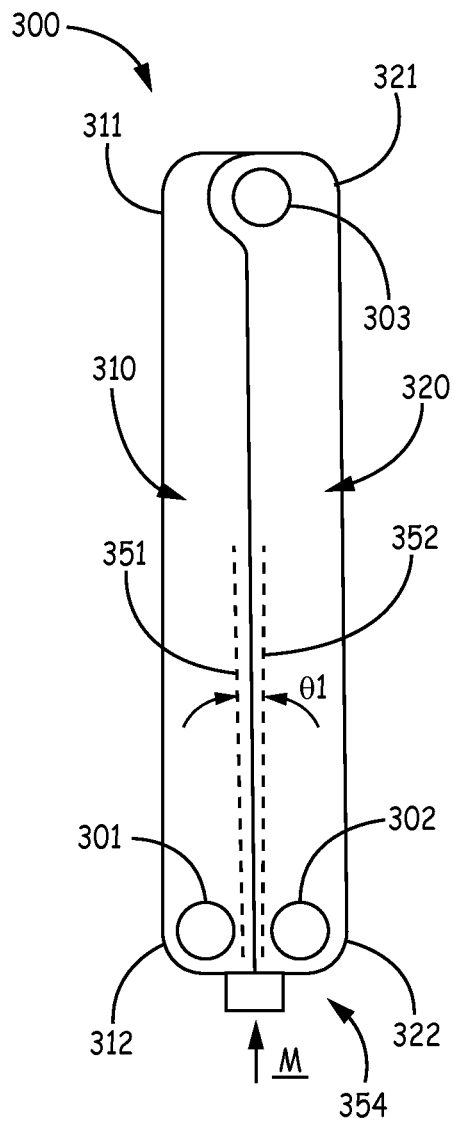
FIG. 3A is an elevation view of an implantable cardiac monitoring device in a relatively compact form, according to some embodiments of the present invention.
Figure 3B:
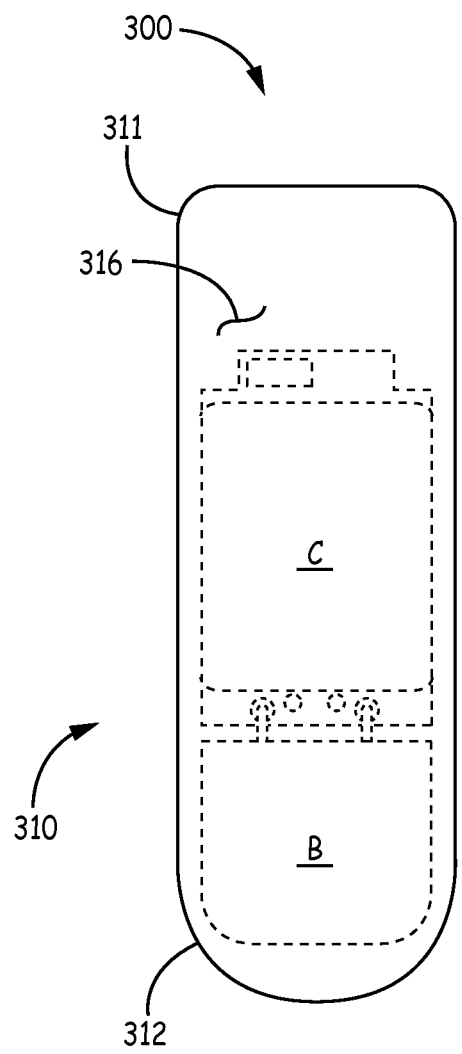
FIG. 3B is a plan view of the device shown in FIG. 3A, according to some embodiments.

FIG. 3A is an elevation view of an implantable cardiac monitoring device 300 in a relatively compact form, according to some embodiments of the present invention; and FIG. 3B is a plan view of the device 300, according to some embodiments. FIG. 3A illustrates device 300 including a first arm 310 and a second arm 320, which are pivotably attached to one another in proximity to first ends 311, 321 thereof, a first electrode 301, which is carried by first arm 310 in proximity to a second end 312 thereof, a second electrode 302, which is carried by second arm 320 in proximity to a second end 322 thereof, and a third electrode 303, which is carried by second arm 320 in proximity to first end 321 thereof. FIG. 3B illustrates first arm 310 of device 300 forming a hermetically sealed housing 316, which contains electronic circuitry C and an associated battery power source B, shown with phantom lines. Electronic circuitry C and battery B may be configured to support sensing by electrodes 301, 302, 303 for electrocardiographic monitoring, according to embodiments and methods known to those skilled in the art, for example, as disclosed in commonly-assigned U.S. Pat. Nos. 5,987,352 and 6,230, 059, which are hereby incorporated by reference.

Housing 316 is preferably formed from titanium, according to methods known in the art, and second arm 320 may be formed from titanium, or another suitable biocompatible metal or relatively rigid polymer. Hermetically sealed feedthroughs (not shown) may be formed through housing 316, also according to known methods, for example, in proximity to first end 311 of arm 310. The feedthroughs, according to an exemplary embodiment, couple each of electrodes 302, 303 to circuitry C, wherein electrode 303 may be directly coupled to a corresponding feedthrough, and electrode 302 coupled to a corresponding feedthrough via an electrically isolated conductive lead (not shown) that is routed along second arm 320. Furthermore, in the exemplary embodiment, housing 316 itself may couple electrode 301 to circuitry C, wherein an insulative overlay, for example, a paralene coating, electrically isolates all of an outer surface of housing 316, except where a conductive surface for electrode 301 is exposed. Those skilled in the art will appreciate and understand a variety of suitable methods for forming electrodes 301-303.

Figure 3D:
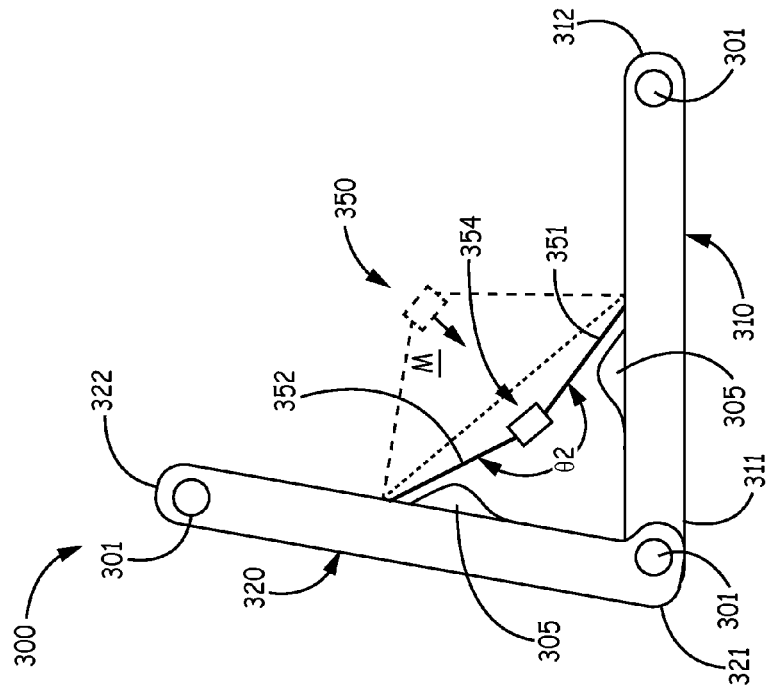
FIGS. 3C-D are a perspective view and an elevation view, respectively, of the device shown in FIGS. 3A-B, in an implant form, according to some embodiments.
Figure 3C:
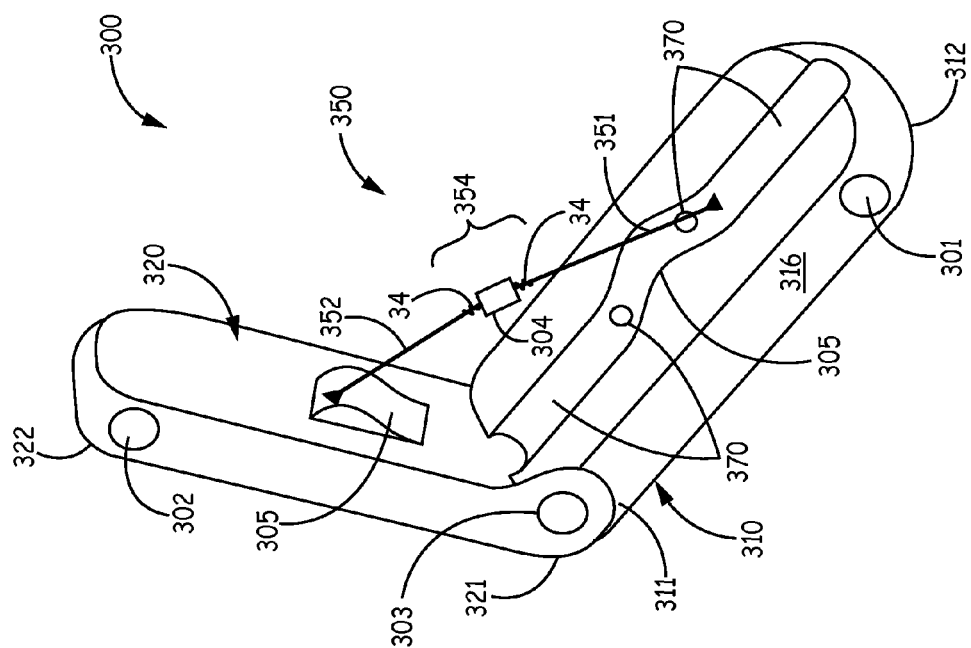

FIGS. 3C-D are a perspective view and an elevation view, respectively, of device 300 in an implant form. FIGS. 3C-D illustrate device 300 including a tether element in the form of a strut 350 attached between arms 310, 320, wherein strut 350 includes a first support member 351, which is pivotably attached to first arm 310, a second support member 352, which is pivotably attached to second arm 320, and a flex-segment 354 joining first and second support members 351, 352 together. FIGS. 3C-D illustrate strut 350 in an expanded state, to support the implant form of device 300, and, with reference back to FIG. 3A, flex-segment 354 allows strut 350 to move from a folded state, at which device 300 is relatively compact, to the expanded state. FIG. 3A illustrates the folded state of strut 350, wherein first and second support members 351, 352 (shown with dashed lines) extend approximately alongside one another, enclosed between arms 310, 320, with flex-segment 354 located in proximity to second ends 312, 322 of arms 310, 320. According to the illustrated embodiment, flex-segment 354, in conjunction with the pivotable attachment of support members 351, 352 to arms 310, 320, allows strut 350 to move, per arrow M, from the folded state to the expanded state. With further reference to FIG. 3C, a channel 370, which is formed in first arm 310, and extends from second end 312 thereof, provides relief for containment of strut support members 351, 352 between arms 310, 320, in the folded state.

FIGS. 3C-D show second ends 312, 322 of arms 310, 320 spaced apart from one another, when strut 350 is in the expanded state, such that electrodes 301, 302, 303 form dual sensing vectors that are approximately orthogonal to one another. According to exemplary embodiments, electrode 301 is spaced apart from electrode 303, along first arm 310, by a distance between approximately 12 mm (0.5 inch) and approximately 10 cm (4 inches), and electrode 302 is spaced apart from electrode 303, along second arm 320, by a similar distance. Thus, the dual sensing vectors formed by electrodes 301, 302, 303, when device 300 is implanted, are useful for generating ECG's and detecting ST segment deviations thereof, as described above, which may be indicative of ischemia in instances of acute myocardial infarction. Yet, the relatively compact form of device 300 (FIGS. 3A-B), for example, having a volume as small as approximately one cubic centimeter and no greater than approximately five cubic centimeters, allows device 300 to be inserted, for subcutaneous implant, through a relatively small incision, which can reduce the incidence of infections and scaring, allow for closure without sutures (e.g. via Steri-strips™), and make the implant procedure less invasive and more suitable for an "in-office" procedure.

FIG. 3C further illustrates flex-segment 354 of strut 350 including an connector portion 304 flanked on either side by a hinge portion 34 that connects each support member 351, 352 to connector portion 304. According to the illustrated embodiment, connector portion 304 may be engaged to move strut 350 from the folded state (FIG. 3A) to the expanded state (FIGS. 3C-D), per arrow M. Strut 350 may be wholly formed from a suitable biocompatible polymer, for example, polypropylene, so that hinge portions 34 can be formed as living hinges, according to methods known in the art. According to some embodiments, strut 350 is formed from a bioabsorbable polymer, for example, a PGA-PLLA (polyglycolide-poly L-lactic acid) copolymer. According to preferred embodiments, support members 351, 352 define an angle θ of between zero degrees and approximately fifteen degrees (θ1 in FIG. 3A) in the folded state, which angle θ opens up to greater than 180 degrees (82 in FIG. 3D) when strut 350 is in the expanded state. (The dotted line in FIG. 3D provides a 180 degree reference.) According to the preferred embodiments, each arm 310, 320 of device 300 may further include an optional abutment feature, for example, like features 305 shown in FIGS. 3C-D, that serve as a stop for support members 351, 352, when moving strut 350 into the expanded state, and may serve to further stabilize strut 350 in the expanded state. Abutment features 305 may be formed integrally with arms 310, 320 or attached thereto.

Figure 4A:
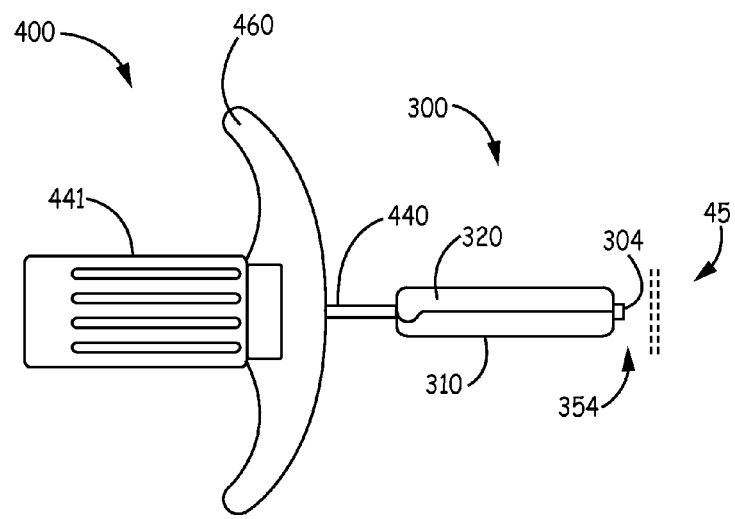
FIG. 4A is a plan view of a tool engaged with the device of FIGS. 3A-D, when the device is in the relatively compact form, according to some embodiments.
Figure 4B:
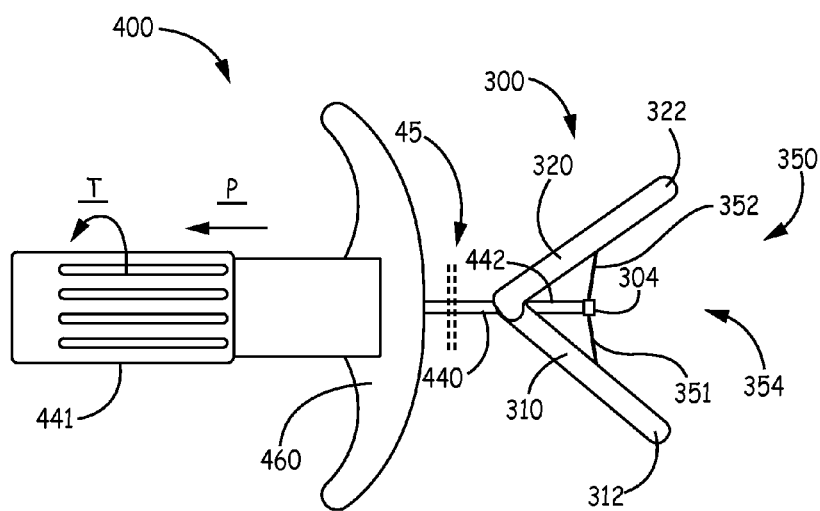
FIG. 4B is a plan view of the tool engaged with the device, after having inserted the device into subcutaneous tissue, according to some embodiments.

Strut 350 may be moved by hand, from the folded to the expanded state, after inserting device 300 through an incision and into subcutaneous tissue, for example, by engaging connector portion 304 of flex-segment 354 with a finger of the hand. Alternately, an implant tool, for example, like tool 400, which is shown in FIGS. 4A-B, may be employed to insert device 300 and then expand strut 350. FIG. 4A is a plan view of a tool 400 engaged with device 300, when the device is in the relatively compact form, according to some embodiments; and FIG. 4B is a plan view of tool 400 engaged with device 300, after having inserted device 300 through an incision 45 and into subcutaneous tissue, according to some embodiments. FIGS. 4A-B illustrate tool 400 including a rod 440, which extends from a proximal end 441 thereof to a distal end 442 thereof, and a handle member 460, which supports rod 440. FIGS. 4A-B further illustrate distal end 442 of rod 440 engaged with connector portion 304 of strut flex-segment 354, for example, via mating threads; and, with reference back to FIG. 3C, the aforementioned channel 370 formed in first arm 310 of device 300 may extend from second end 312, through abutment feature 305, and to first end 311 of first arm 310, to allow rod 440 to extend between first and second arms 310, 320 and engage with flex-segment 354. FIG. 4A shows tool 400 and engaged device 300 in proximity to incision 45, for insertion therethrough and into subcutaneous tissue, for example, by applying a force against handle member 460 of tool 400. Once inserted through incision 45, FIG. 4B shows proximal end 441 of rod 440 having been pulled, per arrow P, according to some methods, to move strut 350 into the expanded state, at which second ends 312, 322 of first and second arms 310, 320 of device 300 are spaced apart from one another and supported by strut 350, as described above. According to the illustrated embodiment, and some methods of the present invention, after moving strut 350 into the expanded state, tool 400 is disengaged from device 300 by applying a torsion force to proximal end 441 of rod 440, to rotate rod 440, per arrow T. Once tool 400 is disengaged from implanted device 300, tool 400 may be removed from the implant site through incision 45. With further reference to the implant form of device 300 shown in FIG. 4B, it may be appreciated that incision 45 is relatively small compared to that which would be required if device 300 were not convertible between the relatively compact form, of FIG. 4A, and the implant form.

Figures 5A, 5B:
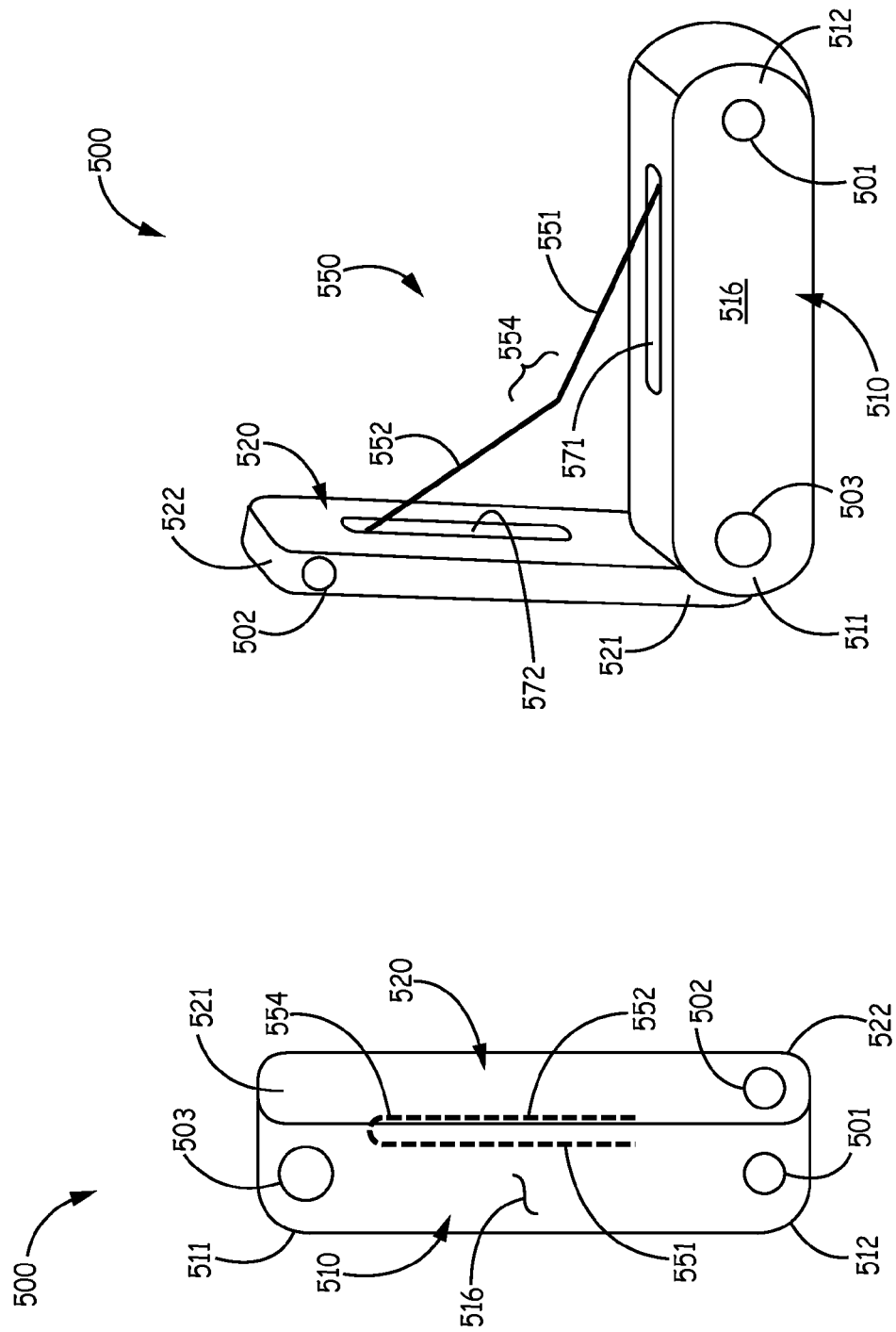
FIG. 5A is an elevation view of an implantable cardiac monitoring device in a relatively compact form, according to some alternate embodiments of the present invention.
FIG. 5B is a perspective view of device shown in FIG. 5A, in an implant form, according to some embodiments.

FIG. 5A is an elevation view of an implantable cardiac monitoring device 500 in a relatively compact form, according to some alternate embodiments of the present invention. FIG. 5A illustrates device 500, similar to device 300, including a first arm 510, a second arm 520, and a plurality of electrodes 501, 502, 503; wherein first ends 511, 521 of arms 510, 520 are pivotably coupled to one another, first electrode 501 is carried by first arm 510, in proximity to a second end 512 thereof, second electrode 502 is carried by second arm 520, in proximity to a second end 522 thereof, and third electrode 503 is carried by second arm 520 in proximity to first end 521 thereof. In the illustrated compact form, device 500 may have a volume of between approximately 1 cubic centimeter and approximately 5 cubic centimeters. First arm 510 of device 500 forms a hermetically sealed housing 516, which contains electronic circuitry and an associated battery power source (not shown), like that described above for device 300, and which includes similar hermetically sealed feedthroughs (not shown) formed therethrough, for example, in proximity to first end 511 thereof. Housing 516, like housing 316 of device 300, may be formed from titanium, and second arm 520, like second arm 320, from titanium, or another suitable biocompatible metal or relatively rigid polymer. Each electrode 501, 502, 503 may be formed and coupled to the circuitry contained within housing 516 in a similar manner to that described above for electrodes 301-303 of device 300.

Figure 5C:
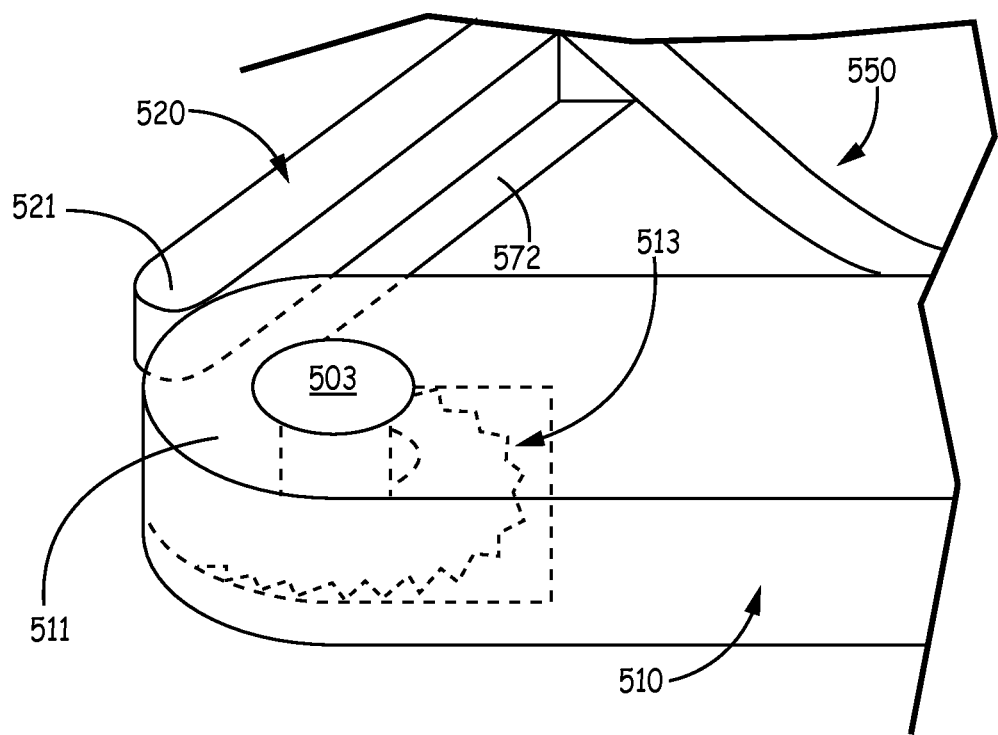
FIG. 5C is an enlarged detail view of a portion of the device of FIGS. 5A-B, according to some embodiments.

FIG. 5B is a perspective view of device 500, in an implant form, according to some embodiments, wherein a tether element 550 is attached between arms 510, 520. According to some embodiments, tether element 550 is a cable, for example, formed from bio-absorbable PGA strands; but, according to the illustrated embodiment, tether element 550 is a strut that includes a first support member 551, which is pivotably coupled to first arm 510, a second support member 552, which is pivotably coupled to second arm 520, and a flex-segment 554, which joins first and second support members 551, 552 together. FIGS. 5A-B illustrate tether element/strut 550 in an expanded state, have been moved from a folded state, which is shown with dashed lines in FIG. 5A. FIGS. 5B-C further illustrate each of first and second arms 510, 520 including an optional channel 571, 572 to provide relief for containment of tether element/cable/strut 550 in the folded state. According to the illustrated embodiment, flex-segment 554 is formed as a spring member, which is biased to move tether element/strut 550 into the expanded state of FIG. 5B, at which second ends 512, 522 of arms 510, 520 are spaced apart from one another and supported by tether element 550. Like device 300, when tether element 550 is in the expanded state, electrodes 501, 502, 503 form dual sensing vectors that are approximately orthogonal to one another, to be useful for generating ECG's and detecting ST segment deviations thereof. The spacing of electrode 501 from 503, along first arm 510, and of electrode 502 from electrode 503, along second arm 520, may be the same as that described above for corresponding electrodes 301-303 of device 300, according to some embodiments.

FIG. 5C is an enlarged detail view of a portion of device 500, according to some embodiments, wherein device 500 further includes an optional ratchet member 513 integrated into the pivotable attachment between first ends 511, 521 of arms 510, 520, to prevent arms 510, 520 from being forced toward one another, against the support of support members 551, 552, when tether element/strut 550 is in the expanded state. According to some embodiments, first end 511 of first arm 510 may be squeezed to release ratchet member 513 and thereby allow arms 510, 520 to be pushed back together so that tether element 550 is moved back into the folded state. It should be noted that such a ratchet member may be integrated into the pivotable attachment of arms 310, 320 of device 300, according to yet further embodiments.

Figure 6A:
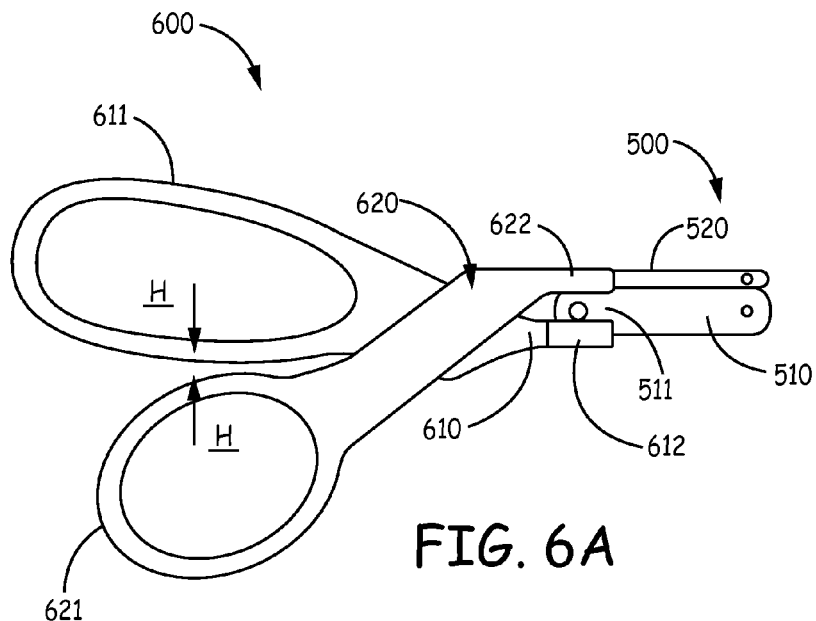
FIG. 6A is a plan view of a tool engaged with the device of FIGS. 5A-B when the device is in the relatively compact form, according to some embodiments.
Figure 6B:
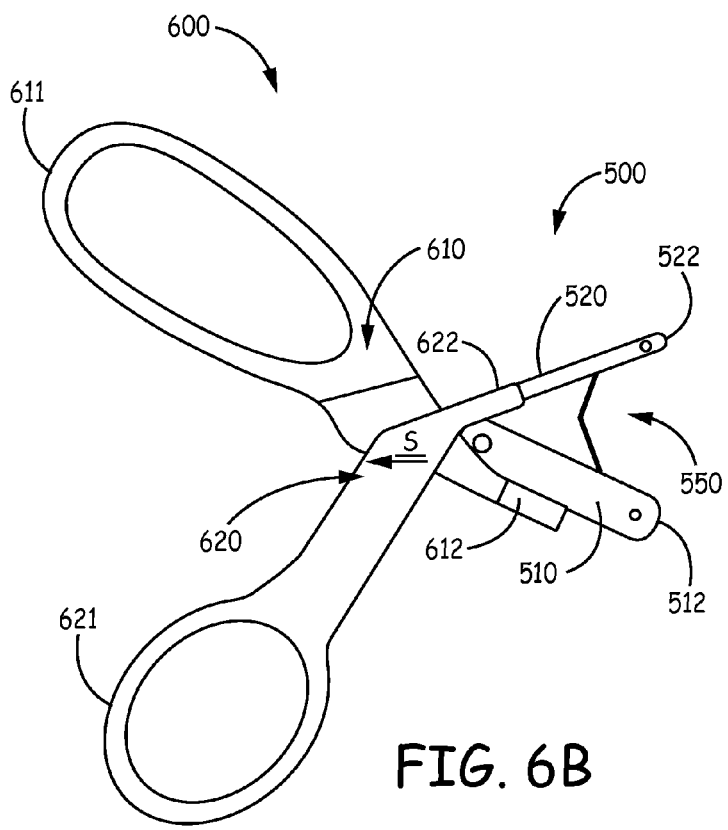
FIG. 6B is a plan view of the tool engaged with the device of FIGS. 5A-B, after having inserted the device into subcutaneous tissue, according to some embodiments.

According to some methods of the present invention, device 500 may be held in the relatively compact form of FIG. 5A, with tether element/strut 550 in the folded state, either by hand, or via a releasable latch (not shown), for example, located in proximity to seconds ends 512, 522 of arms 510, 520, while device 500 is inserted through an incision for implant in subcutaneous tissue; after which device 500 is released to allow the spring bias of flex-segment 554 to move tether element/strut 550 into the expanded state of FIG. 5B. According to some alternate methods and embodiments, a tool, for example, like tool 600 of FIGS. 6A-B may be used to implant device 500. FIG. 6A is a plan view of tool 600 engaged with device 500, when the device is in the relatively compact form; and FIG. 6B is a plan view of tool 600 engaged with device 500, after having inserted device 500 through incision 45 and into subcutaneous tissue. FIGS. 6A-B illustrate tool 600 including first and second tong elements 610, 620 pivotably attached to one another so as to be moveable between a first, closed position (FIG. 6A) and a second, open position (FIG. 6B). According to the illustrated embodiment, first tong element 610 includes an end 612 that is configured to engage first arm 510 of device 500, and second tong element 620 includes an end 622 that is configured to engage second arm 520 of device 500.

With reference to FIG. 6A, opposite ends 611, 621 of each tong element 610, 620 are held together, per arrows H, in order to hold tether element/strut 550 of device 500 in a folded state, thereby keeping arms 510, 520 together in the relatively compact form. According to some methods, while tong elements 610, 620 of tool 600 hold device 500 in the compact form, device 500 is inserted through an incision and into subcutaneous tissue, after which, tool 600 is slid away from device 500, per arrow S of FIG. 6B, and the holding force on ends 611, 621 of tong elements 610, 620 is released to allow the spring bias to move tether element/strut 550 into the expanded state.

In the foregoing detailed description, the invention has been described with reference to specific embodiments. However, it may be appreciated that various modifications and changes can be made without departing from the scope of the invention as set forth in the appended claims.

The invention claimed is:

1. An implantable cardiac monitoring device comprising:
a first arm and a second arm, each arm extending from a first end thereof to a second end thereof, the arms being pivotably attached to one another in proximity to the first ends thereof, and one of the arms forming a hermetically sealed housing;
a plurality of electrodes, a first electrode of the plurality being carried by the first arm in proximity to the second end thereof, a second electrode of the plurality being carried by the second arm in proximity to the second end thereof, and a third electrode of the plurality being carried by one of the arms in proximity to the first end thereof;
electronic circuitry and an associated a power source coupled to the plurality of electrodes for electrocardiographic monitoring, the circuitry and power source being contained within the hermetically sealed housing formed by the one of the arms; and
a tether element attached between the first and second arms;
wherein the tether element is movable between a folded state and an expanded state;
when the tether element is in the folded state, the second ends of the arms are located in close proximity to one another, and the device has a relatively compact form; and
when the tether element is in the expanded state, the second ends of the arms are spaced apart from one another and supported by the tether element, and the electrodes form dual sensing vectors arranged approximately orthogonal to one another.

2. The device of claim 1, wherein:
the tether element comprises a strut, the strut including a first support member, a second support member, and a flex-segment joining the first support member to the second support member, the first support member being pivotably attached to the first arm, and extending from the first arm to the flex-segment, and the second support member being pivotably attached to the second arm, and extending from the second arm to the flex-segment; and
the tether element is moveable between the folded and expanded states by virtue of the flex-segment and the pivotable attachment of each of the support members.

3. The device of claim 2, wherein the support members of the strut define an angle between zero degrees and approximately fifteen degrees, when the strut is in the folded state, and the angle opens up to greater than approximately 180 degrees, when the strut is moved to the expanded state.

4. The device of claim 2, wherein:
each of the arms includes an abutment feature located in proximity to the attachment of the corresponding support member of the strut; and
each of the support members rests against the abutment feature of the corresponding arm when the strut is in the expanded state.

5. The device of claim 2, wherein the flex-segment of the strut is configured to engage with a tool for pulling the flex-segment toward the first ends of the arms, thereby moving the strut to the expanded state.

6. The device of claim 5, wherein the flex-segment comprises a connector portion configured to engage with the tool and a living hinge portion that connects each support member to the engagement portion.

7. The device of claim 2, wherein the flex-segment of the strut comprises a spring member, the spring member being biased to move the strut into the expanded state.

8. The device of claim 1, further comprising a ratchet member integrated into the pivotable attachment of the first ends of the arms, the ratchet member configured to prevent the arms from being forced toward one another, when the strut is in the expanded state.

9. The device of claim 1, wherein the tether element is formed from a bio-absorbable material.

10. The device of claim 1, wherein a length of both the arms is between approximately 2.5 cm (1 in) and approximately 10 cm (4 in), and a volume of the device, when the strut is in the folded state, is between approximately 1 cc and approximately 5 cc.

11. A system for positioning dual sensing vectors subcutaneously, the sensing vectors for cardiac monitoring, and the system comprising:
an implantable cardiac monitoring device comprising:
a first arm and a second arm, each arm extending from a first end thereof to a second end thereof, the arms being pivotably attached to one another in proximity to the first ends thereof, and one of the arms forming a hermetically sealed housing;

a plurality of electrodes, a first electrode of the plurality being carried by the first arm in proximity to the second end thereof, a second electrode of the plurality being carried by the second arm in proximity to the second end thereof, and a third electrode of the plurality being carried by one of the arms in proximity to the first end thereof;

electronic circuitry and an associated a power source coupled to the plurality of electrodes for electrocardiographic monitoring, the circuitry and power source being contained within the hermitically sealed housing formed by the one of the arms; and a strut including a first support member, a second support member, and a flex-segment joining the first support member to the second support member, the first support member being pivotably attached to the first arm, and extending from the first arm to the flex-segment, and the second support member being pivotably attached to the second arm, and extending from the second arm to the flex-segment, the strut being movable between a folded state and an expanded state, the second ends of the arms being located in close proximity to one another, when the strut is in the folded state, so the device has a relatively compact form, and the second ends of the arms being spaced apart from one another and supported by the strut, when the strut is in the expanded state, so the plurality of electrodes form the dual sensing vectors; and a tool configured to engage the device, in the relatively compact form, and to push the engaged device through an incision and into subcutaneous tissue.

12. The system of claim 11, wherein:
the flex-segment of the strut of the device is configured for the engagement by the tool;
the tool comprises an elongate rod extending from a proximal end thereof to a distal end thereof, the distal end being configured to engage the flex-segment of the strut, and the proximal end being configured for application of a pull force and a torsion force to the rod, the pull force moving the strut from the folded state to the expanded state, and the torsion force disengaging the distal end of the rod from the flex-segment.

13. The system of claim 12, wherein:
the support members of the strut of the device define an angle between zero degrees and approximately fifteen degrees, when the tool engages the device in the relatively compact form; and
the angle opens up to greater than approximately 180 degrees, when the pull force applied to the rod of the engaged tool moves the strut to the expanded state.

14. The system of claim 12, wherein:
each of the arms of the device includes an abutment feature located in proximity to the attachment of the corresponding support member of the strut; and
each of the support members rests against the abutment feature of the corresponding arm when the strut is in the expanded state.

15. The system of claim 11, wherein:
the tool comprises a first tong element configured to engage the first arm of the device and a second tong element configured to engage the second arm of the device, the tong elements being pivotably attached to one another to be movable from a first, closed position to a second, open position;
the flex-segment of the strut of the device comprises a spring member, the spring member being biased to move the strut into the expanded state; and
the tong elements of the tool, when closed, hold the strut of the device in the folded state, against the spring bias of the flex-segment.

16. The system of claim 15, wherein the device further comprises a ratchet member integrated into the pivotable attachment of the first ends of the arms, the ratchet member configured to prevent the arms from being forced toward one another, against the support of the strut, when the strut is in the expanded state.

17. A method for positioning dual sensing vectors subcutaneously, the sensing vectors for cardiac monitoring, and the method comprising:
inserting a device, in a relatively compact form, through an incision and into subcutaneous tissue, the device including a first arm, a second arm, and a plurality of electrodes, the arms being pivotably attached to one another in proximity to first ends thereof, a first electrode of the plurality being carried by the first arm in proximity to a second end thereof, a second electrode of the plurality being carried by the second arm in proximity to a second end thereof, and a third electrode of the plurality being carried by one of the arms in proximity to the first end thereof;
moving a strut of the inserted device from a folded state to an expanded state, the strut being pivotably attached to the arms such that the second ends of the arms are located in close proximity to one another, when the strut is in the folded state, and the second ends of the arms are spaced apart from one another and supported by the strut, when the strut is in the expanded state; and
wherein the plurality of electrodes form the sensing vectors when the strut is moved into the expanded state.

18. The method of claim 17, further comprising engaging a flex-segment of the strut with a distal end of an elongate member prior to inserting the device, the flex-segment joining a first support member of the strut to a second support member of the strut, the first support member being pivotably attached to the first arm, and the second support member being pivotably attached to the second arm; and wherein moving the strut comprises pulling on the flex-segment with the elongate member.

19. The method of claim 18, wherein pulling on the flex-segment opens up an angle, which is defined between the support members of the strut, from between zero degrees and approximately fifteen degrees to greater than approximately 180 degrees.

20. The method of claim 18, further comprising disengaging the elongate member from the flex-segment, after moving the strut to the expanded state, by applying a torsion force the elongate member.

* * * * *